(12) United States Patent
Zemp et al.

(10) Patent No.: US 11,061,124 B2
(45) Date of Patent: Jul. 13, 2021

(54) SYSTEM AND METHOD FOR ULTRASOUND IMAGING

(71) Applicant: The Governors of the University of Alberta, Edmonton (CA)

(72) Inventors: Roger Zemp, Edmonton (CA); Christopher Ceroici, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 748 days.

(21) Appl. No.: 15/792,422

(22) Filed: Oct. 24, 2017

(65) Prior Publication Data

US 2018/0164418 A1    Jun. 14, 2018

Related U.S. Application Data

(60) Provisional application No. 62/411,003, filed on Oct. 21, 2016.

(51) Int. Cl.
*G01S 7/52*     (2006.01)
*A61B 8/00*    (2006.01)
(Continued)

(52) U.S. Cl.
CPC ........ *G01S 7/52025* (2013.01); *A61B 8/4477* (2013.01); *A61B 8/4488* (2013.01);
(Continued)

(58) Field of Classification Search
CPC ............... G01S 7/5202; G01S 7/52023; G01S 7/52025; G01S 7/52046; G01S 7/52079;
(Continued)

(56) References Cited

U.S. PATENT DOCUMENTS

| 4,448,075 A | 5/1984 | Takemura et al. |
| 4,570,488 A | 2/1986 | Miwa et al. |

(Continued)

FOREIGN PATENT DOCUMENTS

WO    2008/033528    3/2008

OTHER PUBLICATIONS

Seo, Chi Hyung, and Jesse T. Yen. "A 256 x 256 2-D array transducer with row-column addressing for 3-D rectilinear imaging." IEEE transactions on ultrasonics, ferroelectrics, and frequency control 56, No. 4 (2009): 837-847.*

(Continued)

*Primary Examiner* — Carolyn A Pehlke
(74) *Attorney, Agent, or Firm* — Nathan V. Woodruff

(57) ABSTRACT

A method of ultrasonically imaging an object includes providing a 2D array of bias-sensitive ultrasound transducer elements. Each ultrasound transducer element has first and second electrodes on first and second sides of the ultrasound transducer connected in plural first and second electrode strips. The plural first electrode strips are oriented at an angle to the plural second electrode strips. A biasing pattern is applied to a plurality of the second electrode strips and generating a series of transmit events in one or more first electrode strips. Return pulses are detected by measuring received signals from biased second electrode strips. For the series of transmit events, the second electrode strips are biased according to sequential biasing patterns of voltages that correspond to rows or columns of an invertible matrix. The measured received signals are processed to generate an image of the object.

20 Claims, 7 Drawing Sheets

(51) Int. Cl.
  *B06B 1/06* (2006.01)
  *A61B 8/08* (2006.01)
  *G01S 15/89* (2006.01)
  *B06B 1/02* (2006.01)

(52) U.S. Cl.
  CPC .......... *A61B 8/4494* (2013.01); *A61B 8/5207* (2013.01); *B06B 1/0207* (2013.01); *B06B 1/0292* (2013.01); *B06B 1/0622* (2013.01); *B06B 1/0662* (2013.01); *G01S 7/5202* (2013.01); *G01S 7/52046* (2013.01); *G01S 7/52079* (2013.01); *G01S 7/52085* (2013.01); *G01S 15/8925* (2013.01); *G01S 15/8993* (2013.01); *G01S 15/8997* (2013.01)

(58) Field of Classification Search
  CPC ............ G01S 7/52085; G01S 15/8925; G01S 15/8993; G01S 15/8997; A61B 8/4477; A61B 8/4483; A61B 8/4488; A61B 8/4494; A61B 8/52; A61B 8/5207; B06B 1/0207; B06B 1/0292; B06B 1/0622; B06B 1/0662
  See application file for complete search history.

(56) References Cited

U.S. PATENT DOCUMENTS

| | | | |
|---|---|---|---|
| 4,580,451 A | 4/1986 | Miwa et al. | |
| 4,671,293 A | 6/1987 | Shaulov | |
| 5,027,820 A | 7/1991 | Pesque | |
| 5,152,294 A | 10/1992 | Mochizuki et al. | |
| 5,167,231 A | 12/1992 | Matsui | |
| 5,327,895 A | 7/1994 | Hashimoto | |
| 5,345,139 A | 9/1994 | Gururaja et al. | |
| 5,396,143 A | 3/1995 | Seyed-Bolorforosh | |
| 5,410,205 A | 4/1995 | Gururaja et al. | |
| 5,460,179 A | 10/1995 | Okunuki et al. | |
| 5,460,181 A | 10/1995 | Seyed-Bolorforosh | |
| 5,488,956 A | 2/1996 | Bartelt et al. | |
| 5,490,512 A | 2/1996 | Kwon | |
| 5,657,295 A | 8/1997 | Howard | |
| 5,671,746 A | 9/1997 | Dreschel et al. | |
| 5,846,201 A | 12/1998 | Adams | |
| 6,381,197 B1 | 4/2002 | Savord et al. | |
| 6,419,633 B1 | 7/2002 | Robinson et al. | |
| 7,087,023 B2 | 8/2006 | Daft et al. | |
| 7,544,165 B2 | 6/2009 | Mamayek | |
| 7,618,373 B2 | 11/2009 | Ladabaum et al. | |
| 7,780,597 B2 | 8/2010 | Panda et al. | |
| 2007/0079658 A1 | 4/2007 | Wagner | |
| 2014/0117809 A1 | 5/2014 | Zemp | |

OTHER PUBLICATIONS

Novell, Anthony, Mathieu Legros, Jean-Marc Grégoire, Paul A. Dayton, and Ayache Bouakaz. "Evaluation of bias voltage modulation sequence for nonlinear contrast agent imaging using a capacitive micromachined ultrasonic transducer array." Physics in Medicine & Biology 59, No. 17 (2014): 4879.*

Jensen, J.A., Nikolov, S. I., Gammelmark, K. L., & Pedersen, M. H.; Synthetic aperture ultrasound imaging. Ultrasonics; 2006; 44, pp. e5-e15.

Zemp, R. J., Sampaleanu, A., & Harrison, T.; S-sequence encoded synthetic aperture B-scan ultrasound imaging; 2013 IEEE International Ultrasonics Symposium (IUS); Jul. 2013 pp. 593-595.

Rasmussen, M. F., & Jensen, J. A.; 3-D ultrasound imaging performance of a row-column addressed 2-D array transducer: A measurement study; 2013 IEEE International Ultrasonics Symposium (IUS); Jul. 2013; pp. 1460-1463.

Sampaleanu, A., Zhang, P., Kshirsagar, A., Moussa, W., & Zemp, R. J.; Top-orthogonal-to-bottom-electrode (TOBE) CMUT arrays for 3-D ultrasound imaging; IEEE transactions on ultrasonics, ferroelectrics, and frequency control; 2014; 61(2), pp. 266-276.

Sampaleanu, A., Zemp R.; Synthetic Aperture 3D Ultrasound Imaging Schemes with S-Sequence Bias-Encoded Top-Orthogonal-to-Bottom-Electrode 2D CMUT Arrays; 2013 IEEE International Ultrasonics Symposium (IUS); 2013 pp. 1994-1997.

* cited by examiner

SYSTEM AND METHOD FOR ULTRASOUND IMAGING

FIELD

This relates to arrays of ultrasound transducers and in particular, systems and methods of controlling the arrays to image an object.

BACKGROUND

Ultrasound imaging using 2D arrays of ultrasonic transducers is useful in obtaining three dimensional images of an object, such as in medical diagnosis. Different types of transducers may be used, such as piezoelectric transducers or capacitive micromachined ultrasound transducers (CMUTs), which offer some potential advantages over piezoelectric transducers.

Fully-wired 2D arrays are cost-prohibitive due to large channel counts. A common difficulty in implementing 2D arrays for 3D ultrasound imaging is the problem of large channel counts. A fully-wired array of N×N elements would require $N^2$ transmit/receive channels, introducing significant system complexity and cost, especially if N is large. Fabrication and interconnect schemes are non-trivial. Capacitive micromachined ultrasound transducers (CMUTs) are miniature membrane structures typically manufactured on silicon wafers using microfabrication technology. They offer a natural solution for 3D imaging, and provide a number of potential advantages over traditional piezoelectric transducer materials including inherently broadband immersion operation for tissue imaging, exceptional sensitivity, and potential for improved mass fabrication and integration with on-chip high density electronics.

Many CMUT designs use a bottom doped wafer as a common ground-plane, while metalized top membranes serve as signal electrodes. Others use the top membrane as the ground plane, however, provide no way of electrically addressing bottom electrodes. These architectures are not amenable to the low-channel-count imaging schemes we propose. One possible architecture is a double-SOI wafer-bonded (D-SOI-WB) architecture, which permits top electrodes to be routed and connected independent of the bottom electrode routing and connection schemes.

SUMMARY

There is provided an ultrasound array comprising plural capacitive micromachined ultrasound transducers (CMUTs), each CMUT having a top electrode and a bottom electrode, the respective top electrodes of the CMUTs being connected in plural top electrode strips (TES), and the respective bottom electrodes of the CMUTs being connected in plural bottom electrode strips (BES), the BES being oriented at an angle to the TES, the angle being substantially different from zero; transmit electronics connected to the TES or BES; and receive electronics connected to the TES or BES.

There is provided in a further embodiment an ultrasound array comprising plural ultrasound transducers, each ultrasound transducer having a top electrode and a bottom electrode, the respective top electrodes of the ultrasound transducers being connected in plural top electrode strips (TES), and the respective bottom electrodes of the ultrasound transducers being connected in plural bottom electrode strips (BES), the BES being oriented at an angle to the TES, the angle being substantially different from zero; control electronics connected to the BES or to the TES, the control electronics controlling the response of the ultrasound transducers; and transmit electronics and transmit electronics connected to the other of the TES or BES.

In various embodiments, there may be included any one or more of the following features: the ultrasound transducers may be capacitive micromachined ultrasound transducers or bias-sensitive piezoelectric transducers; and the control electronics may control the response of the ultrasound transducers by controlling bias and or modulation voltages.

According to an aspect, there is provided a method of ultrasonically imaging an object comprises the steps of: providing a 2D array of bias-sensitive ultrasound transducer elements, each ultrasound transducer element having a first electrode on a first side of the ultrasound transducer and a second electrode on a second side of the ultrasound transducer, the respective first electrodes being connected in plural first electrode strips, and the respective second electrodes being connected in plural second electrode strips, the plural first electrode strips being oriented at an angle to the plural second electrode strips, the angle being substantially different from zero; applying a biasing pattern to a plurality of the second electrode strips and generating a series of transmit events in one or more first electrode strips; detecting return pulses by measuring received signals from biased second electrode strips; wherein, for the series of transmit events, the second electrode strips are biased according to sequential biasing patterns of voltages that correspond to rows or columns of an invertible matrix; and processing the received signals to generate an image of the object.

According to other aspects, the method may comprise one or more of the following elements, alone or in combination: the series of transmit events may be coupled to more than one first electrode strips, and for each transmit event, transmission signals to each electrode strip may be timed to generate an electronically-steerable cylindrical elevational focus; processing the received signals may comprise using the inverse of the invertible matrix to calculate an equivalent synthetic aperture dataset comprising effective isolated transmit signals and reception for each second electrode strip followed by synthetic aperture beamforming such that the image has two-way focusing in a direction parallel to the first electrode strips, and the image being one-way focused in a direction parallel to the second electrode slips; the first electrode strips may be orthogonal to the second electrode strips; the polarity and amplitude of the emitted signals from each element may be dependent on the polarity and strength of the respective bias voltages; measuring the received signals may comprise decoupling a received AC signals from the bias, and for a negative bias, the polarity of the received AC signal may be reversed; the sensitivity of the ultrasound transducer may be related to the bias voltage; a further series of transmit events may be applied to the second electrode strips and measuring received signals from the first electrode strips; the second electrode strips may be biased with the biasing pattern when the return pulses are measured; the ultrasound transducers may comprise capacitive micromachined ultrasonic transducers or bias-sensitive piezoelectrics; the matrix may be a Hadamard matrix or an S-matrix or other invertible matrix.

According to an aspect, there is provided an ultrasound imaging system comprising a 2D array of bias-sensitive ultrasound transducer elements, each ultrasound transducer element having a first electrode on a first side of the ultrasound transducer and a second electrode on a second side of the ultrasound transducer, the respective first electrodes being connected in plural first electrode strips, and the respective second electrodes being connected in plural second electrode strips, the plural first electrode strips being oriented at an angle to the plural second electrode strips, the angle being substantially different from zero; a controller connected to the first and second electrode strips. The controller is programmed to: apply a biasing pattern to a plurality of the second electrode strips and generate a series of transmit events in one or more first electrode strips; detect return pulses by measuring received signals from biased second electrode strips; wherein, for the series of transmit events, the second electrode strips are biased according to sequential patterns of voltages that correspond to rows or columns of an invertible matrix; and process the received signals to generate an image of the object.

According to other aspects, the system may comprise one or more of the following elements, alone or in combination: the controller may be programmed to couple the series of transmit events to more than one first electrode strips, and for each transmit event, to time transmission signals to each electrode strip to generate an electrically steerable cylindrical elevational focus; the controller may be programmed to process the received signals using the inverse of the invertible matrix to calculate an equivalent synthetic aperture dataset comprising effective isolated transmit signals and reception for each second electrode strip followed by synthetic aperture beamforming such that the image has two-way focusing in a direction parallel to the first electrode strips, and the image being one-way focused in a direction parallel to the second electrode slips; the first electrode strips may be orthogonal to the second electrode strips; the first and second electrodes may comprise top and bottom electrodes or bottom and top electrodes; the ultrasound transducers may comprise capacitive micromachined ultrasonic transducers or bias-sensitive piezoelectrics; there may be bias tees for decoupling a received AC signal from the bias for each received signal; the second electrode strips may be biased with the biasing pattern when the return pulses are measured; and the matrix may be a Hadamard matrix or an S-matrix or other invertible matrix.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which:

In FIG. 11(a), y=0 imaging-plane and FIG. 11(b), y=1 mm imaging plane.

DETAILED DESCRIPTION

Figure 1:
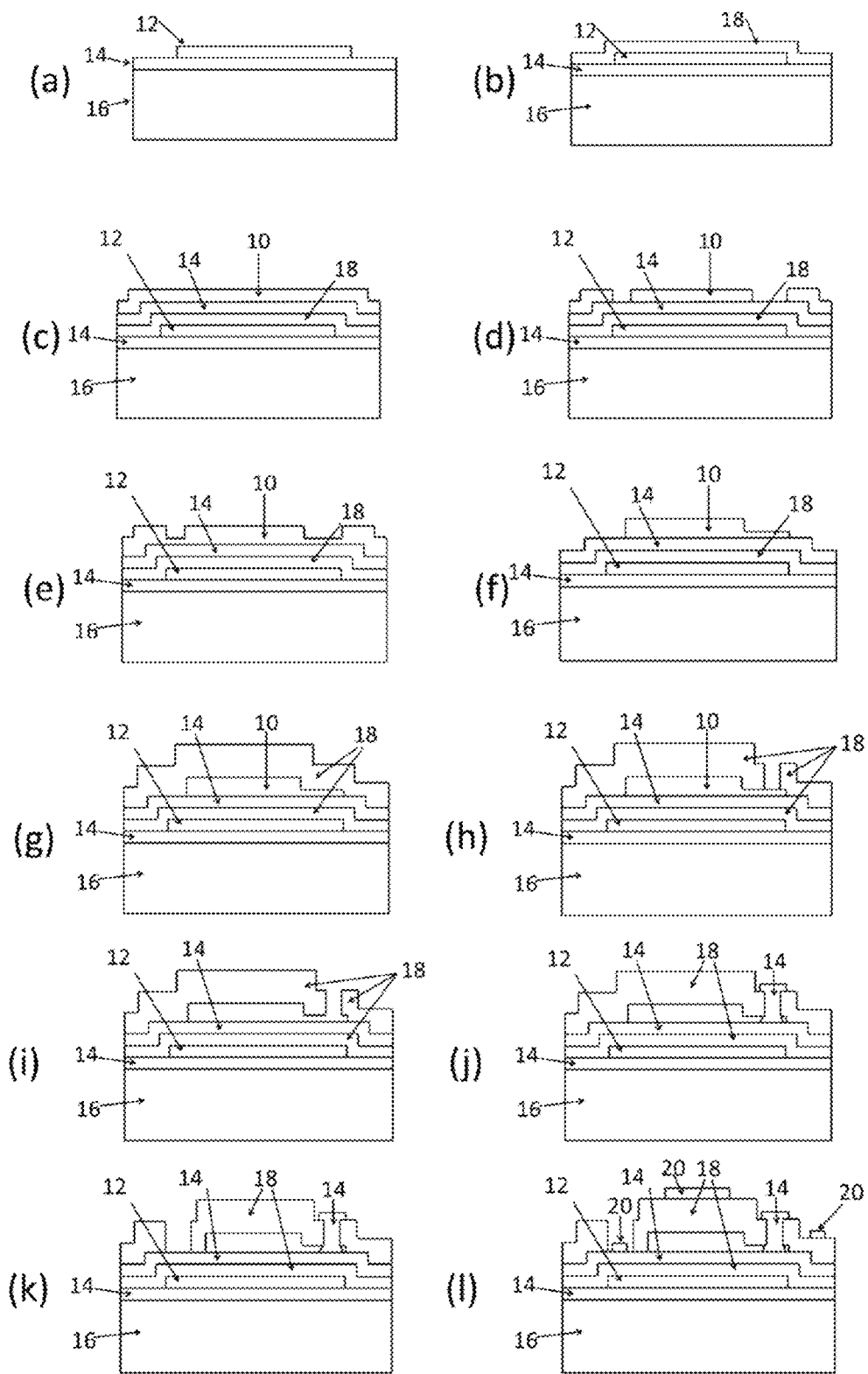
FIGS. 1(a)-(l) is a sequence of side views showing a patterned-SOI sacrificial release process (P-SOI-SR) fabrication process.

An example of a 2D array will now be described with respect to FIG. 1 through 11.

The 2D array designs may be implemented using a D-SOI-WB architecture, or other possible architectures. One possible embodiment is presented, based on a modified sacrificial release fabrication scheme: one using a patterned SOI wafer with doped device-layer serving as bottom electrode.

TOBE 2D CMUT arrays permit 3D ultrasound imaging using N transmit channels and N receive channels rather than $N^2$ transmit/receive channels. Two imaging schemes will be described by way of examples of the behavior and use of a CMUT array. The first scheme permits 3D image formation with only N transmit events, but provides only one-way focusing, whereas the second scheme permits 2-way focusing but requires $N^2$ transmit events, similar to mechanically-wobbled linear arrays, but without the need for mechanical scanning. The first scheme permits the top electrode to serve as ground (beneficial for patient safety) but this is not possible in the second scheme, hence a passivation layer would be required. An additional imaging scheme will then be presented that addresses some deficiencies in the first two schemes.

Capacitive micromachined ultrasound transducers (CMUTs) offer many potential advantages over piezoelectric transducers, and hold promise for cost-effective 2D arrays. Fully-wired 2D arrays are cost-prohibitive due to large channel counts. We present what we call Top-Orthogonal-to-Bottom Electrode (TOBE) 2D CMUT arrays with the potential to perform 3D imaging with an N×N 2D array using only N transmit channels and N receive channels. Candidate fabrication technologies are discussed and a modified sacrificial release process is used to fabricate a prototype.

There will be discussed a scheme for obtaining an image, either 2D or 3D, of an object using ultrasonic transducers, such as the CMUT architecture discussed herein, with only N transmit channels and N receive channels. The CMUT architectures permits independent addressability of both top and bottom CMUT electrodes. CMUT top electrodes are connected in strips along the x-direction, while CMUT bottom electrodes are connected in strips along the y-direction.

CMUT Architectures and Fabrication

Aspects of the CMUT architectures discussed herein include (1) top electrodes that are addressable and connected separately and independently from bottom electrodes, which have their own connectivity and (2) top electrodes that are connected in strips, with bottom electrodes connected in strips in the orthogonal direction from top electrode strips. The CMUT architecture may include a double-SOI wafer-bonded (D-SOI-WB) architecture similar as is known in the art. This architecture permits top electrodes to be routed and connected independent of the bottom electrode routing and connection schemes. The 2D array designs discussed herein may be implemented using this double-SOI CMUT architecture. An alternate architecture may also be used that is based on a modified sacrificial release fabrication scheme: one using a patterned SOI wafer with doped device-layer serving as bottom electrode. This process may be referred to as a patterned-SOI sacrificial-release process (P-SOI-SR). In either process (D-SOIWB or P-SOI-SR), top electrodes may be connected in strips which are orthogonal to bottom electrode strips. Alternate fabrication schemes are possible to realize embodiments of the TOBE architecture described here as would be understood by a person of average skill in the art.

FIG. 1 shows the P-SOI-SR fabrication scheme. In FIG. 1 (a)-(l), the process is shown using the materials PolySi 10, heavily boron doped silicon 12, $SiO_2$ 14, silicon 16, $Si_3N_4$ 18, and aluminum 20. An SOI wafer with boron-doped device layer is patterned using high etch-rate (up to 32 μm/min) inductively-coupled plasma deep reactive etching (ICPDRIE) (Alcatel AMS200) in (a) to define bottom electrodes with the buried oxide (BOX) layer serving as an etch-stop. Then LPCVD nitride is deposited in (b) as a bottom dielectric layer and KOH-etch-stop. LPCVD oxide is next deposited in (c) and will act as an etch-stop layer for ICP-RIE etching of the nitride layers. LPCVD PolySi is next deposited in (c) as a sacrificial layer. This is patterned to define the gap-area in (d). Another LPCVD PolySi deposition in (e) and patterning step (f) provides definition of low-height etching channels, while slightly increasing the height of the sacrificial PolySi in the gap area. BOE etching is performed in (f) to remove the oxide layer in all areas except directly below the gap and etching-channel PolySi areas. This is done so that when nitride top membranes are deposited in (g), the nitride will act as a KOH etch-stop layer. If this BOE step were not performed KOH etching could slowly etch the oxide layer and thus slowly erode the CMUT sidewalls to a larger than desired extent. On the other hand, if the oxide layer were not present, there would be no ICP-DRIE etch-stop layer, and over-etching into the bottom SOI wafer could be catastrophic.

For the top membrane structural material a sandwich structure is proposed: a few nm of stoichiometric $Si_3N_4$ then a thick layer of low-stress (<100 MPa) LPCVD nitride, then a final few nm of stoichiometric $Si_3N_4$. The KOH etch selectivity between polySi (fast etching) and nitride (negligible etching) is higher for stoichiometric compared to low-stress nitride with our films, and these thin layers will not significantly add to the membrane stress. High etch-selectivity is important because our membranes can be larger than 100 microns across for low-frequency devices, and erosion of the nitride material could be catastrophic if KOH etch-selectivity were low. After sandwich nitride layers are deposited in (g), then sacrificial etching holes are formed (h) in the nitride layers down to the oxide etch-stop layer using ICP-DRIE. Sacrificial etching is next performed in (i) using KOH wet-etching until membranes are released. Although the etch-rate of oxide is much slower than PolySi, the oxide layer beneath the gap and etch-channel areas will be completely etched away during the long sacrificial etches. There is danger of H2 release during KOH etching rupturing large membranes and there is danger of membrane stiction during drying—especially for large membrane (>100 microns-wide) structures. Membranes as large as 82 μm-wide (2 MHz resonant frequency in air) were successfully etched and released without problems. Etch holes are sealed in (j) using low-stress PECVD TEOS which forms sealing plugs without coating CMUT gap. The gap would be coated if LPCVD were used, which has conformal coating. The TEOS is removed everywhere except the etch-hole region with a BOE etch step. This is done to prevent differing dielectric layers in the membrane as this could be a source of charge-trapping due to Maxwell Capacitor surface-charge accumulation at the dielectric interface. Additionally, there is no need to make the membrane any thicker than necessary, and a thick layer of TEOS is preferred to ensure sealing reliability and to maintain vacuum hermaticity long-term. CMUT cavity formation and sealing is complete after this step. Next, an access hole to the bottom electrode is formed in (k) by ICP-DRIE. This step may etch into the device layer (which is several microns thick) but this is inconsequential as the device layer is doped throughout the entire thickness. Finally metallization and patterning is performed in (l) to form the top membrane, top interconnects, top electrode bond-pad, and bottom-electrode bond-pad. With this design, wafer-level testing is easy to perform and the complexity of through-wafer-vias is avoided.

This process is similar to but different than the original sacrificial release fabrication schemes. Advantages of this method include an etch-stop for each important etching step, permitting high-etch-rate high-throughput ICP-DRIE to be used in an industrial fab without optimizing the etch-depths and without worrying about consequences of overetching. This P-SOI-SR architecture also permits independent patterning of top and bottom electrodes, key to the success of the proposed device.

Figure 2:
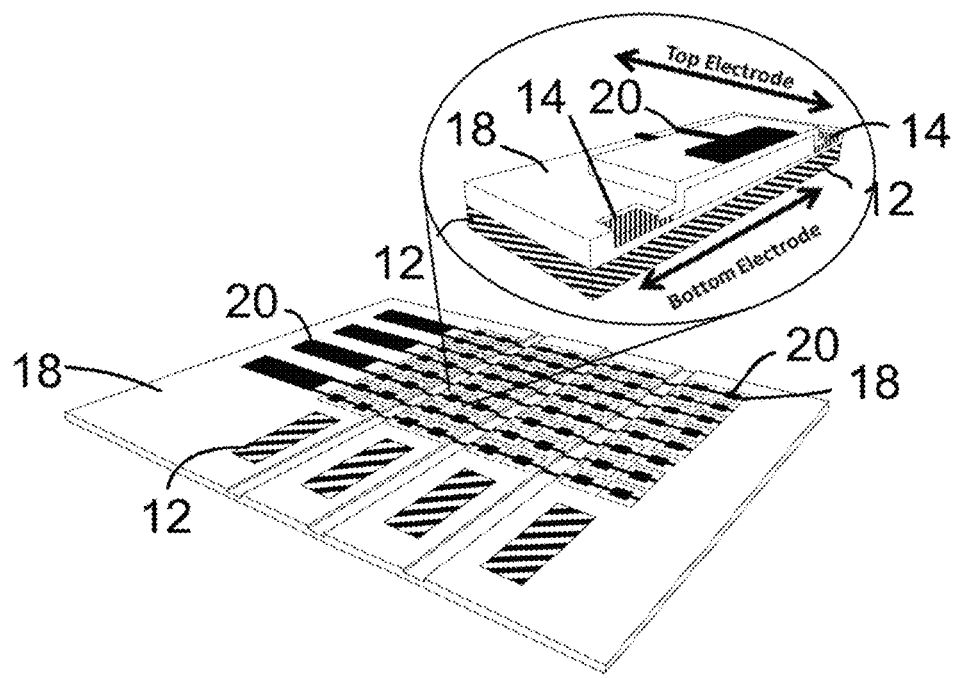
FIG. 2 is a perspective view showing the TOBE 2D CMUT array structure.

Each element in the 2D array structure may include arrays of CMUT cavities, such as 1×1, 2×2, 3×3, etc. Top electrodes are connected in strips orthogonal to bottom electrode strips as shown in FIG. 2. This structure design may be referred to as a Top Orthogonal-to-Bottom-Electrode Strip 2D CMUT array (TOBE-2D CMUT array). Materials used are labeled with reference characters as in FIG. 1.

Imaging Schemes

Figure 3:
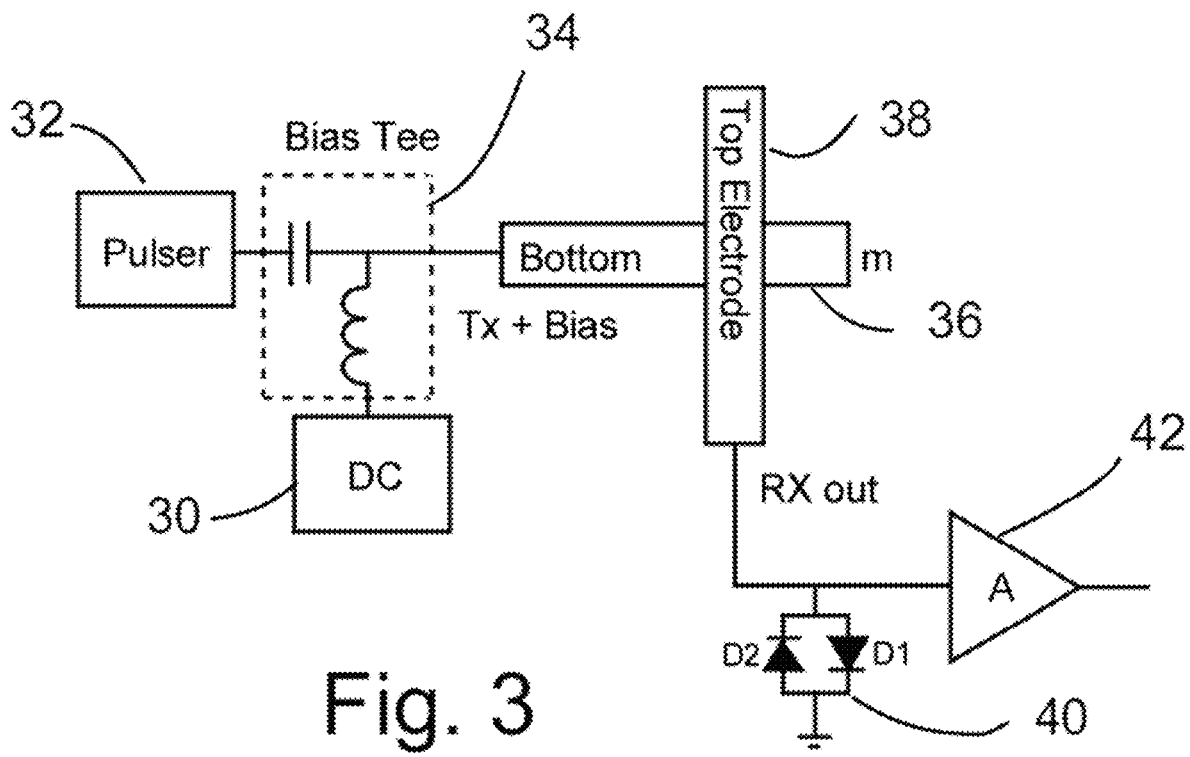
FIG. 3 is a schematic diagram showing a first imaging scheme where the top electrode serves as ground and routes receive signals to an amplifier. The diode pair prevents voltages greater than 0.7V from existing between the CMUT and a patient.

In one example, 3D imaging may be accomplished using hybrid piezo-polymer/PZT arrays, where horizontal strips of PZT are used to transmit ultrasound, while vertical strips of PVDF are used to receive ultrasound. With this method, one-way focusing in the x-direction and one-way focusing in the y-direction may be accomplished. This scheme is implementable in straightforward way using the TOBE-2D-CMUTs, as illustrated in FIG. 3. In this scheme, which may be referred to as orthogonal one-way dynamic transmit-receive focusing (O1-DTRF) operation, bias voltages from DC source 30 and pulses from pulser 32 via bias tee 34 are applied to the bottom electrode strips 36, while the top electrode 38 is maintained at ground via a diode pair 40 for electrical safety to prevent any voltages greater than 0.7V from contacting a human subject. While passivation layers can also be used, this scheme provides electrical safety, yet also permits small <0.7V receive signals be received via the top electrode and be amplified by amplifier 42. Alternate electronics may also be used to provide bias voltages and transmit-receive signals.

Figure 4:
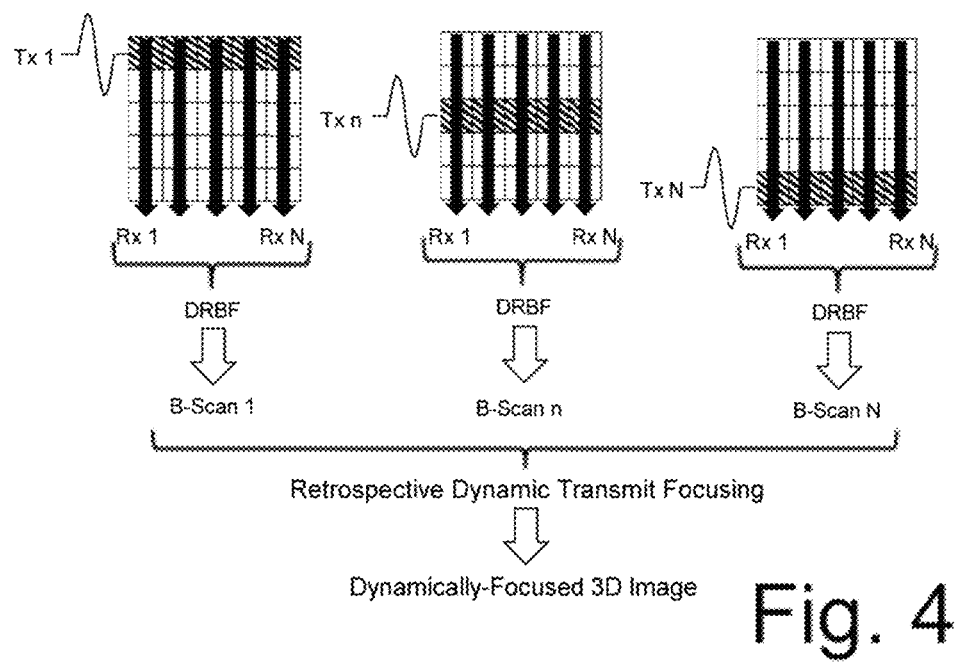
FIG. 4 is a schematic diagram showing Orthogonal One-way Dynamic Transmit-Receive Focusing (O1-DTRF). DRBF: Dynamic Receive Beamforming. Tx: Transmit. Rx: Receive.

FIG. 4 is a schematic diagram showing Orthogonal One-way Dynamic Transmit-Receive Focusing (O1-DTRF). DRBF: Dynamic Receive Beamforming. Tx: Transmit. Rx:

Receive. To form 3D images, bottom transmit strips are excited one at a time. Signals received by vertical top electrodes are received in parallel and beam formed to form B-scans using dynamic-receive beamforming. Once all transmit strips have been fired and an RF B-scan formed for each transmit event, the RF-B-scans can then be subjected to retrospective dynamic transmit-beamforming to produce an image focused in both x- and y-directions.

Using this approach, a 3D image may be formed using only N transmit events, and with N transmit channels and N-receive channels. One disadvantage of this scheme is that only one-way x-focusing and one-way y-focusing may be implemented. Additionally, single element control is not possible for more complex imaging schemes.

Figure 5:
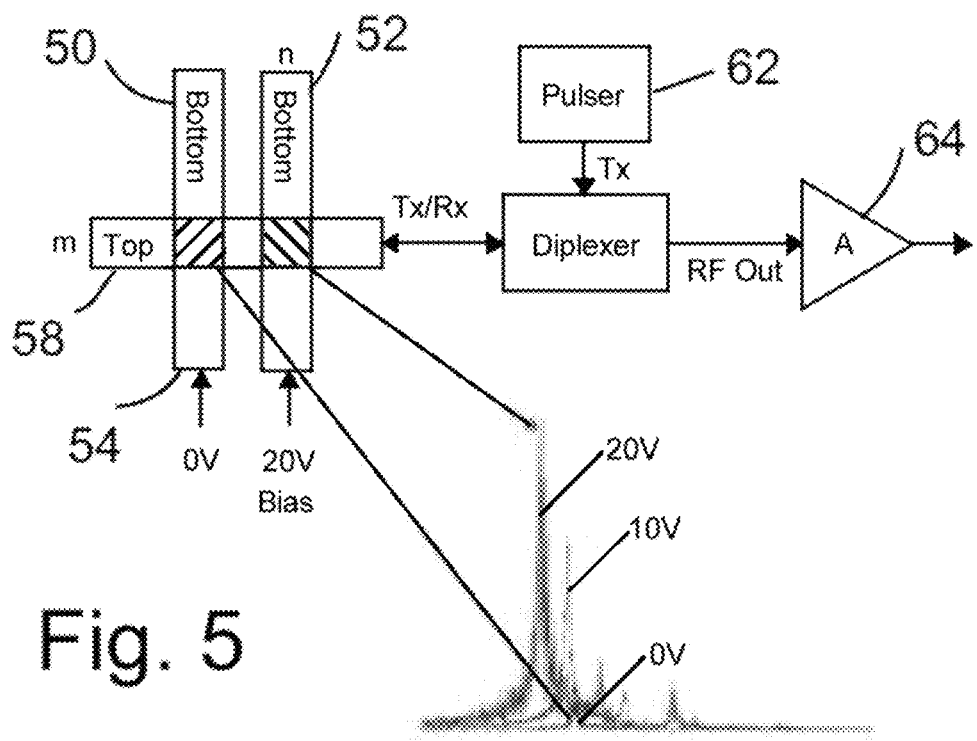
FIG. 5 is a schematic diagram showing a second imaging scheme where the top electrodes route transmit (Tx) and receive (Rx) signals, while the bottom electrode serves as bias voltage control. The response of the CMUT with a bias voltage is significantly greater (~9×) that when no bias voltage is used.

Another imaging scheme may be used, as represented by FIG. 5, in which bottom electrodes 50 and 52 provide bias voltage control, with bottom electrode 50 being supplied with first bias voltage 54 (0V in the embodiment shown) and bottom electrode 52 being supplied with second bias voltage 56 (20V in the embodiment shown), while top electrodes 58 are used for routing both transmit and receive signals, accomplished via a diplexer 60. A pulser 62 is connected to the diplexer, and an amplifier 64 is also connected to the diplexer. In this interfacing scheme, it is not possible to maintain the top electrode at ground potential using the present embodiment and a passivation layer will be required to provide electrical isolation for patient electrical safety. Even if the passivation layer is compromised, however, top electrode signals will contain single-cycle MHz-frequency burst signals with low-duty-cycle and low average power that should not pose a significant shock hazard to patients compared to lower frequencies. Alternate electronics may also be used to provide bias voltages and transmit receive signals.

Figure 6:
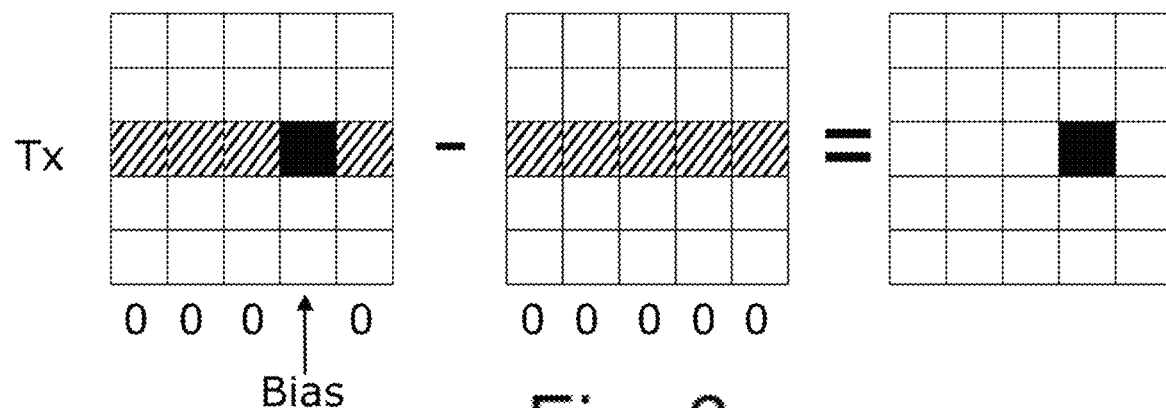
FIG. 6 is a schematic diagram showing a method to use the second scheme for single element control.
Figure 7:
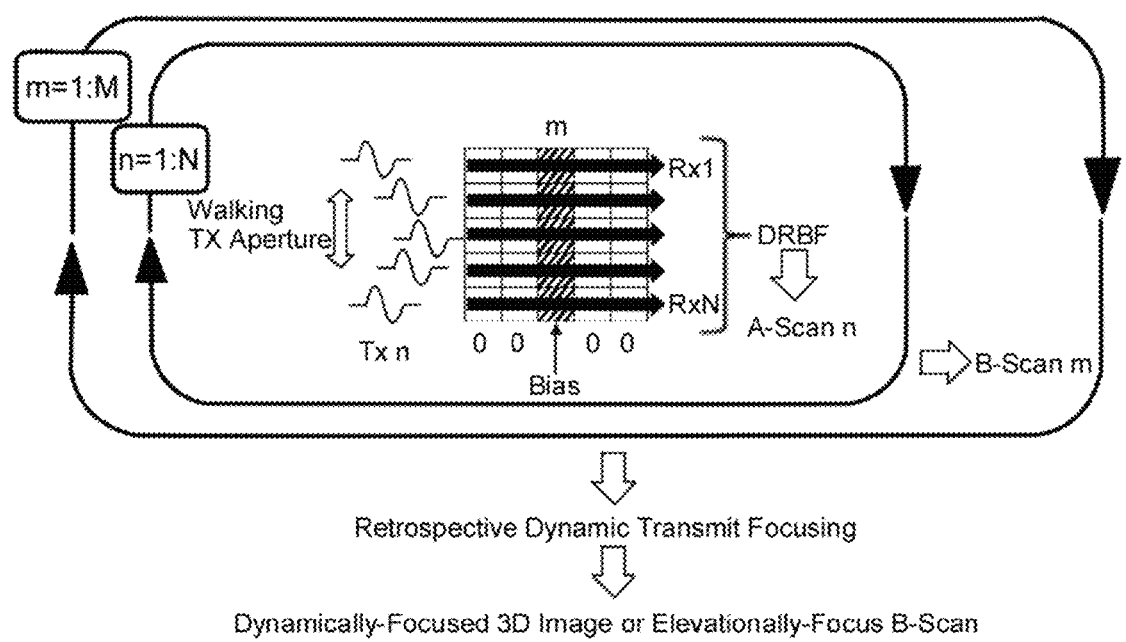
FIG. 7 is a schematic diagram showing Orthogonal 2-Way Dynamic Transmit-Receive Focusing using the second scheme.

This control scheme makes use of the nonlinear transmit and receive response of CMUTs as a function of the bias voltage. With zero bias voltage, a given transmit pulse will produce negligible membrane oscillation. However, when a bias voltage is applied that is near the collapse voltage (for pre-collapse operation) or above the collapse voltage (for collapse-mode operation) the transmit response can be significantly higher. This is illustrated in FIG. 5, where real vibrometer testing data (to be discussed later) has been incorporated into the illustrative schematic. With the interconnect methodology of this scheme, it is possible to principally excite one element across a strip while other elements have negligible excitation. If we then consider two transmit events along the same strip: one with a bias applied to one vertical strip (with zero elsewhere) and another with zero bias on all strips, we may subtract the measured response from the two transmit events to effectively simulate a transmit event from a single element. This now is very powerful because groups of elements can be used to transmit and receive with different transmit or receive delays. Unlike the O1-DTRF method described above where only one-way focusing is possible in each direction, two-way focusing is possible in this scheme, if an imaging pulse sequence pictorially illustrated in FIG. 6 is used. This methodology may be referred to as orthogonal 2-way dynamic transmit-receive focusing (O2-DTRF). Enhanced resolution and lower sidelobes of O2-DTRF come at the expense of more transmit events (but similar to that used in a wobbled linear array probe) compared with O1-DTRF. Both schemes, however, require only N transmit channels and N receive channels. Multiplexing could further reduce the required channel count at the expense of requiring more transmit events, which could reduce frame-rate and lead to more motion artifacts. FIG. 7 is a schematic diagram showing O2-DTRF. Many additional imaging pulse- and bias-sequences may be implemented to perform imaging based on the proposed TOBE architecture and interfacing schemes.

It was found that one disadvantage of this imaging scheme is that only a single column is active at a time, and there is no active transmit focusing in the lateral direction resulting in a low signal-to-noise ratio. An additional problem lies in the fact that since only one element per row is active at a time, parasitic capacitance from interconnects could swamp the small capacitance of the elements without careful engineering. This could result in additional signal-to-noise degradation, compounding the problem.

To address this difficulty, a coded aperture pulse sequence may be used with the potential to significantly improve signal-to-noise ratio. This method is similar to O2-DTRF but uses coded biasing patterns so that more than one column contributes to active transmitter and receiver area. This involves firing focused pulses along rows to produce an elevational focus, and during each transmit event applying a biasing pattern to columns. Signals are received in parallel along rows to enable dynamic-receive beamforming in the elevation direction. After firing multiple transmit events using a complete set of biasing patterns, selected from an S-Matrix or Hadamard Matrix, the data can be unmixed to obtain the effective signal associated with transmitting along individual columns. This reconstructed dataset is then subjected to synthetic aperture retrospective receive beamforming to form a 3D image with 2-way elevational focusing but only 1-way lateral focusing. This scheme offered improved signal-to-noise over O2-DTRF since more than one column is actively transmitting at a time, thus leading to improved emitted energy. However, $O\{N^2\}$ transmit events are required to form a 3D image, and more disconcertingly, $O\{N^2\}$ transmit events are required to even form a two-way focused B-scan.

Another imaging scheme, which may be described as Fast Orthogonal Row-Column Electronic Scanning (FORCES) will now be described. This FORCES TOBE imaging scheme may be used to obtain B-scan image quality comparable to a linear array transducer but with the flexibility to perform electronic 3D scanning. Row- and column addressing can be switched, for example to transmit along columns and receive along rows to obtain fast y-z B-scans. By quickly switching imaging orientations one may acquire fast x-z and y-z orthogonal imaging planes. Alternatively, multiple B-scans can be scanned to form a volumetric 3D image.

Figure 8:
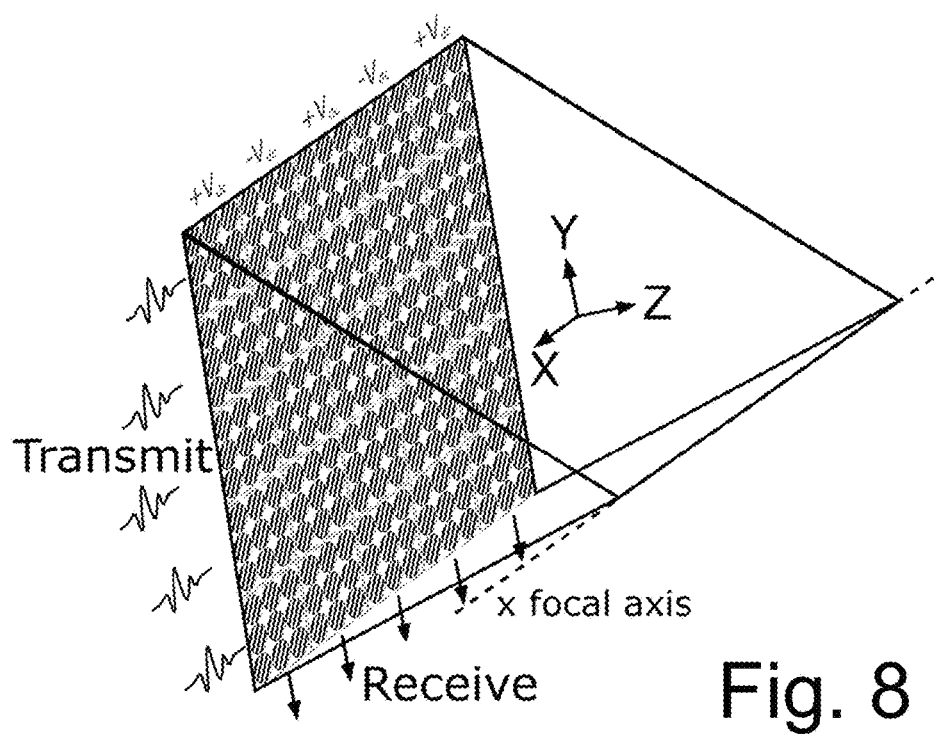
FIG. 8 is a schematic of a Fast Orthogonal Row-Column Electronic Scanning (FORCES) imaging scheme.
Figure 9:
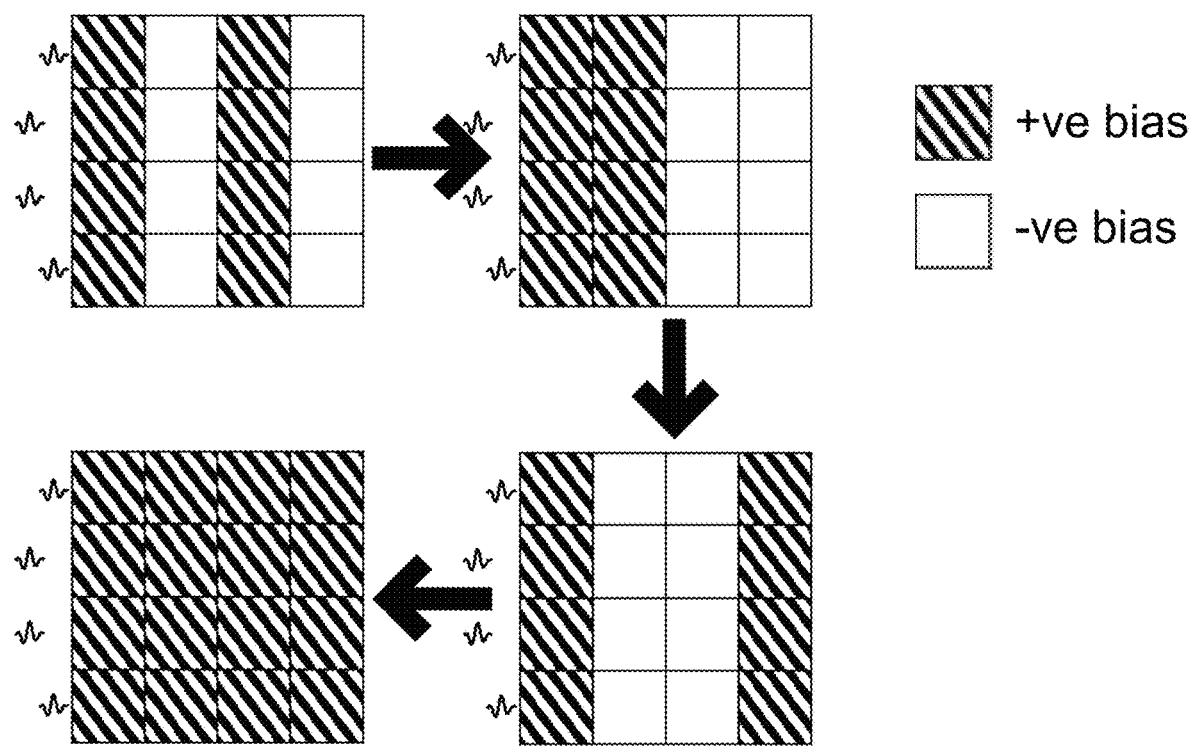
FIG. 9 is an illustration of a transmit column bias sequence for a 4×4 TOBE array with positive and negative biases applied to different columns.

In the proposed FORCES scheme, focused pulses are transmitted along rows while biasing columns. However, instead of receiving along rows, signals are received along columns in parallel, where the columns have been biased using key biasing patterns. Transmit focusing enables fixed-cylindrical elevational focusing, as shown in FIG. 8. Multiple transmit events may be used with a stitching algorithm to improve elevational depth of focus. For each transmit event, a biasing pattern is applied to columns. The biasing pattern may include positive voltages, negative voltages, and voltages of different magnitude as the sensitivity of the transducer may relate to the magnitude of the biasing voltage. When data is received from columns, AC signals are decoupled from DC biases using, for example, bias tees 34 as shown in FIG. 3. When AC signal from columns are received in parallel, they may be dynamically beamformed for one-way lateral focusing. Additional lateral focusing power can be achieved by retrospective synthetic transmit focusing. This is accomplished by using a sequence of biasing patterns selected from an S-Matrix, Hadamard Matrix, or other invertible matrix, as shown in FIG. 9. By decoding, we obtain an effective synthetic transmit aperture dataset associated with effectively transmitting with one column at a time and receiving on all. This reconstructed dataset is then subjected to synthetic aperture focusing to create images that offer two-way focusing laterally but with only one-way static elevation focusing. In comparing FORCES with O2-DTRF, the FORCES imaging scheme allows a B-scan may be formed with ≤N transmit events with one-way elevational focusing and two-way in-plane lateral resolution. This allows for an image to be obtained more quickly with a higher image quality, while still providing the functionality for electronically-scanned 3D imaging. This functionality could then be extended to very large 2D arrays, potentially as large as an entire wafer.

Simulations

Figure 11A:
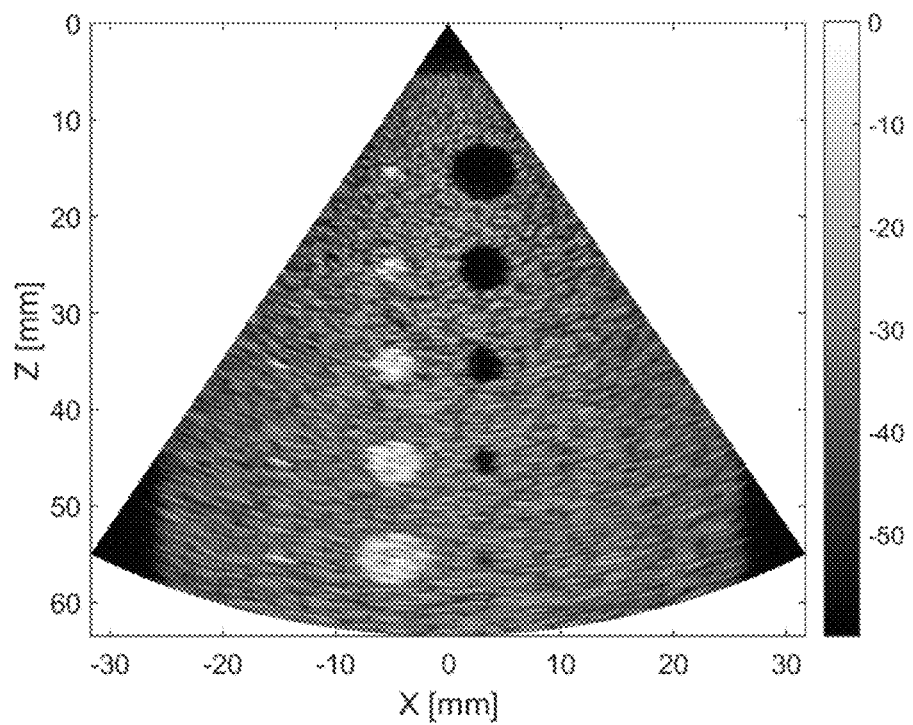
FIG. 11(a) and (b) are scattering phantom simulated images using FORCES TOBE imaging scheme.
Figure 11B:
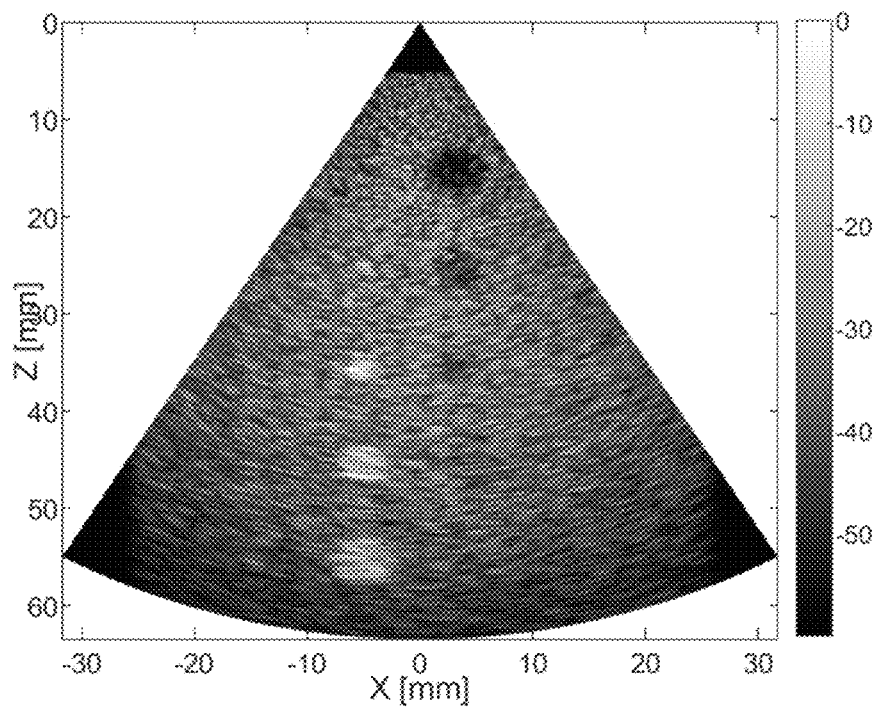

To demonstrate the potential of the proposed FORCES TOBE imaging technology, we perform Field II simulations. We model 64×64 TOBE arrays with 110 μm×110 μm elements having 5.8 μm kerfs and a center frequency of 6.67 MHz. This provides an array with $\lambda/2$ pitch. We binned columns in groups of 2 to reduce the number of transmit events. We simulated point targets and a scattering phantom and used 4 elevational transmit focal zones. An image for each x-z B-scan was created for each elevational focus, and the B-scans were stitched together to form a single x-z B-scan using a Gaussian weighting function. To form a single x-z B-scan, delay times were calculated for each row and each y-z focal point to define the elevational slice. The column biases were sampled from rows of a Hadamard matrix. The received scattered signals were summed across each column. After 32 transmit events (each with a separate bias-encoding), we decoded using the inverse Hadamard Matrix to recover the synthetic aperture dataset. Synthetic transmit aperture imaging was accomplished using a beamforming toolkit developed by Svetslav Nikolov. Images from different elevational slices are shown in FIG. 11 to demonstrate the 3D capabilities of the proposed imaging technique.

Figure 10:
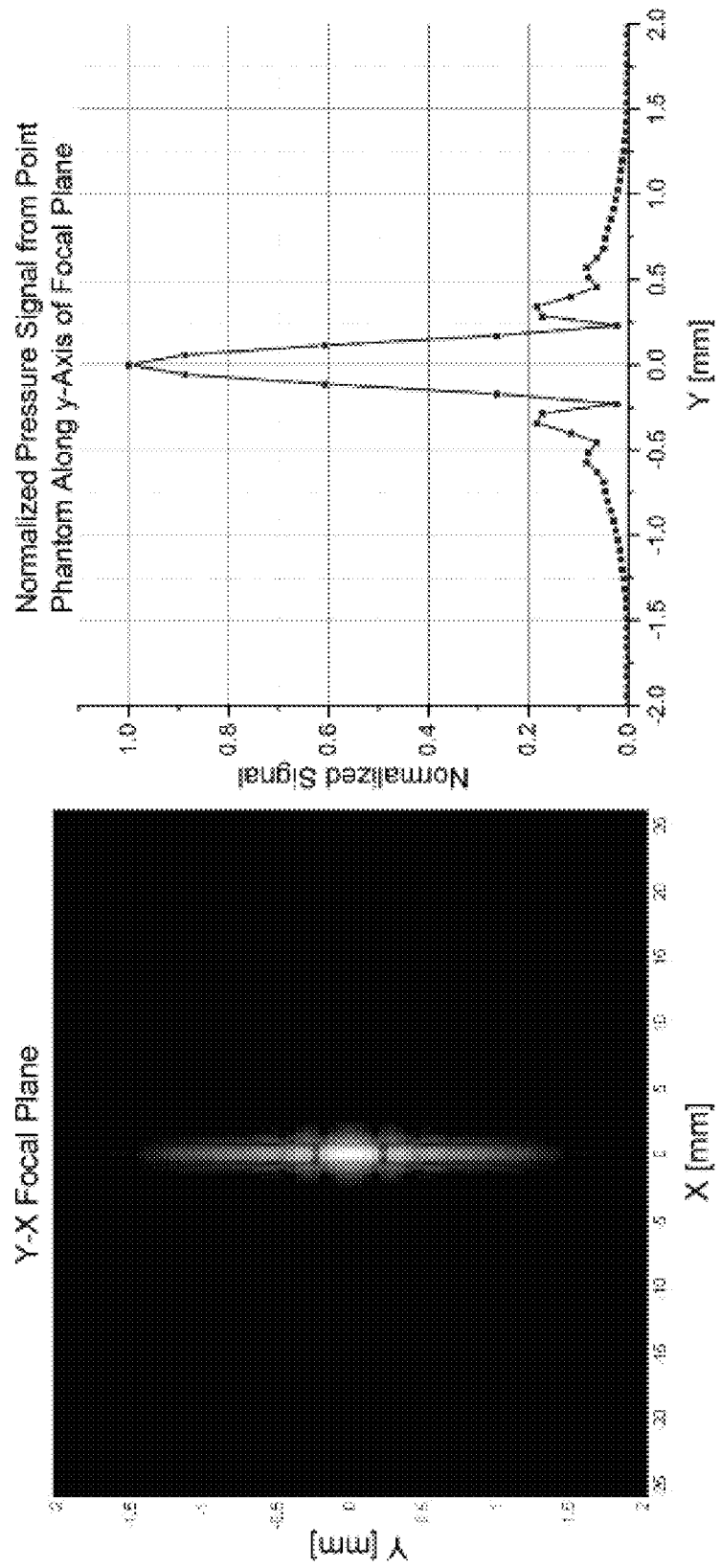
FIG. 10 is a point-phantom x-y C-scan maximum amplitude projection image (left) and accompanying elevational point-spread function profile (right) of an image obtained using FORCES.

To investigate the elevation focusing capabilities of the FORCE TOBE imaging scheme, we used point target phantom simulations. FIG. 10 shows an x-y maximum amplitude projection C-scan image of a point target located at 30 mm depth. The elevational focus is not as tight as the lateral focus but provide reasonable slice selection for x-z B-scan imaging.

To investigate the 3D imaging capabilities of the FORCES TOBE imaging scheme we performed simulated imaging of a scattering phantom with wire-targets, spherical hyper-echoic targets, and spherical cysts of various sizes. The y=0 image-plane image, formed with 4 different transmit focal zones is shown in FIG. 11(*a*). A slice at y=1 mm is shown in FIG. 11(*b*). Clearly, as the image plane slides across the cyst phantoms, the cyst visibility decreases and the wire targets are no longer visible. These encouraging results could form the basis of more advanced 3D imaging capabilities.

Discussion

In the proposed FORCES TOBE imaging scheme, a B-scan can be formed with two-way focused in-plane lateral resolution, and because each transmit event is accompanied by in-plane dynamic receive focusing, each transmit event can produce a low-resolution image. The sum of multiple low-resolution images will yield a high-resolution image as per previous synthetic aperture imaging methods. To image fast columns may be binned together to produce an effectively course transmit array. This would sacrifice lateral transmit focusing quality, however, this can be compensated for with dynamic receive focusing. Elevational sectioning may suffer unless multiple transmit focal zones are used.

Although the example given uses perpendicular electrode sets, which is preferred in practice, in principle so long as the electrodes are at a sufficient non-zero angle to yield a useful signal, the electrode sets need not be exactly orthogonal. There needs however to be some degree of orthogonality, that is, a non-zero angle between the electrode sets. It should also be mentioned that when we refer to electrodes or electrode strips, this may mean conductive material is routed between electrodes of individual elements. It may also be generalized to include active or passive elements used to route elements together. These strips need not be monolithic with the transducers and may be implemented using a number of means.

Immaterial modifications may be made to the embodiments described here without departing from what is covered by the claims. In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

What is claimed is:

1. A method of ultrasonically imaging an object, comprising the steps of:
   providing a 2D array of bias-sensitive ultrasound transducer elements, each ultrasound transducer element having a first electrode on a first side of the ultrasound transducer element and a second electrode on a second side of the ultrasound transducer element, the respective first electrodes being connected in plural first electrode strips, and the respective second electrodes being connected in plural second electrode strips, the plural first electrode strips being substantially non-parallel to the plural second electrode strips;
   applying a biasing pattern to a plurality of the second electrode strips and generating a series of transmit events in one or more first electrode strips;
   detecting return pulses by measuring received signals from biased second electrode strips;
   wherein, for the series of transmit events, the second electrode strips are biased according to sequential biasing patterns of voltages that are derived from rows or columns of an invertible matrix having at least one negative entry;
   measuring received signals by decoupling AC signals from the biased second electrode strips, wherein a polarity of at least one received signal corresponding to the at least one negative entry is reversed; and
   processing the received signals to generate an image of the object.

2. The method of claim 1, wherein the series of transmit events are coupled to more than one first electrode strips, and for each transmit event, transmission signals to each electrode strip are timed to generate an electronically-steerable cylindrical elevational focus.

3. The method of claim 1, wherein processing the received signals comprises the steps of:
   using the inverse of the invertible matrix to calculate an equivalent synthetic aperture dataset comprising effective isolated transmit signals and reception for each second electrode strip; and applying synthetic aperture beamforming to the equivalent synthetic aperture dataset such that the image has two-way focusing in a direction parallel to the first electrode strips, and the image being one-way focused in a direction parallel to the second electrode strips.

4. The method of claim 1, wherein the first electrode strips are orthogonal to the second electrode strips.

5. The method of claim 1, wherein the polarity and amplitude of an emitted signal from each element during a transmit event is dependent on the polarity and strength of the respective bias voltages.

6. The method of claim 1, further comprising the step of, for a negative bias, reversing the polarity of the AC signals.

7. The method of claim 1, wherein the sensitivity of each ultrasound transducer element is related to the bias voltage.

8. The method of claim 1, further comprising the step of applying a further series of transmit events to the second electrode strips and measuring received signals from the first electrode strips.

9. The method of claim 1, wherein the second electrode strips are biased with the biasing pattern when the return pulses are measured.

10. The method of claim 1, wherein the ultrasound transducer elements comprise capacitive micromachined ultrasonic transducers or bias-sensitive piezoelectrics.

11. The method of claim 1, wherein the matrix is a Hadamard matrix or an S-matrix.

12. An ultrasound imaging system comprising:
a 2D array of bias-sensitive ultrasound transducer elements, each ultrasound transducer element having a first electrode on a first side of the ultrasound transducer element and a second electrode on a second side of the ultrasound transducer element, the respective first electrodes being connected in plural first electrode strips, and the respective second electrodes being connected in plural second electrode strips, the plural first electrode strips being substantially non-parallel-to the plural second electrode strips;
a decoupler for decoupling the AC signal from the bias to obtain a received signal;
a controller connected to the first and second electrode strips, the controller being programmed to:
apply a biasing pattern to a plurality of the second electrode strips and generate a series of transmit events in one or more first electrode strips;
detect return pulses by measuring received signals from biased second electrode strips, wherein, for the series of transmit events, the second electrode strips are biased according to sequential patterns of voltages that are derived from rows or columns of an invertible matrix having at least one negative entry;
invert at least one received signal corresponding to the at least one negative entry; and
process the received signals to generate an image of the object.

13. The system of claim 12, wherein the controller is programmed to couple the series of transmit events to more than one first electrode strips, and for each transmit event, to time transmission signals to each electrode strip to generate an electrically steerable cylindrical elevational focus.

14. The system of claim 12, wherein the controller is programmed to:
process the received signals using the inverse of the invertible matrix to calculate an equivalent synthetic aperture dataset comprising effective isolated transmit signals and reception for each second electrode strip; and
applying synthetic aperture beamforming to the equivalent synthetic aperture dataset such that the image has two-way focusing in a direction parallel to the first electrode strips, and the image being one-way focused in a direction parallel to the second electrode strips.

15. The system of claim 12, wherein the first electrode strips are orthogonal to the second electrode strips.

16. The system of claim 12, wherein the first and second electrodes comprise top and bottom electrodes or bottom and top electrodes.

17. The system of claim 12, wherein the ultrasound transducer elements comprise capacitive micromachined ultrasonic transducers or bias-sensitive piezoelectrics.

18. The system of claim 12, wherein the second electrode strips are biased with the biasing pattern when the return pulses are measured.

19. The system of claim 12, wherein the matrix is a Hadamard matrix or an S-matrix.

20. The system of claim 12, wherein the controller is further programmed to, for a negative bias, reverse the polarity of the received AC signal.

* * * * *